United States Patent [19]

Stemmer

[11] Patent Number: 5,514,568

[45] Date of Patent: May 7, 1996

[54] ENZYMATIC INVERSE POLYMERASE CHAIN REACTION

[75] Inventor: Willem P. C. Stemmer, Carlsbad, Calif.

[73] Assignee: Eli Lilly and Company, Indianapolis, Ind.

[21] Appl. No.: 184,751

[22] Filed: Jan. 19, 1994

Related U.S. Application Data

[63] Continuation of Ser. No. 691,140, Apr. 26, 1991, abandoned.

[51] Int. Cl.$^6$ .............................. C12P 19/34; C12Q 1/68; C12Q 1/70; C07H 21/04
[52] U.S. Cl. .................. 435/91.2; 435/6; 435/5; 536/24.33; 935/78
[58] Field of Search .................. 435/6, 91.2, 5; 536/24.33

[56] References Cited

U.S. PATENT DOCUMENTS

| | | | |
|---|---|---|---|
| 4,800,159 | 1/1989 | Mullis et al. | 435/91.2 |
| 4,935,357 | 6/1990 | Szybalski | 435/91.2 |
| 4,959,312 | 9/1990 | Sirotkin . | |
| 5,023,171 | 6/1991 | Ho et al. | 435/6 |

OTHER PUBLICATIONS

Hermes, et al. "A Reliable Method for Random Mutagensis: The Generation of Mutant Libraries Using Spiked Oligodeoxyribonucleotide Primers" Gene 84: 143–151 (1989).

Hemsley et al., A simple method for site–directed mutagensis using the polymerase chain reaction, Nucleic Acids Research 17:6545–6551 (1989).

Jones, D. H. and Howard, B. H., A Rapid Method for Site–Specific Mutagensis and Directional Subcloning by Using the Polymerase Chain Reaction to Generate Recombinant Circles, BioTechniques 8:178–183 (1990).

Jones, D. H. and Howard, B. H., A Rapid Method for Recombiantion and Site–Specific Mutagenesis by Placing Homologous Ends on DNA Using Polymerase Chain Reaction, BioTechniques 10:62–66 (1991).

Saiki et al., Primer–Directed Enzymatic Amplification of DNA with a Thermostable DNA Polymerase, Science 239: 487–491 (1988).

Higuchi et al., A general method of in vitro preparation and specific mutagenesis of DNA fragments: study of protein and DNA interactions, Nucleic Acids Research 16:7351–7367 (1988).

Nelson, R. M., and Long, G. L., A General Method of Site–Specific Mutagenesis Using a Modification of the Thermus aquaticus Polymerase Chain Reaction, Analytical Biochemistry 180:147–151 (1989).

Tomic, et al. Nucl. Acids Res. 18(6):1656 (1990).

Primary Examiner—W. Gary Jones
Assistant Examiner—Lisa Arthur
Attorney, Agent, or Firm—Knobbe, Martens, Olson & Bear

[57] ABSTRACT

The invention is directed to a method of introducing at least one predetermined change in a nucleic acid sequence of a double-strand DNA. The method includes: (a) providing a first primer and a second primer capable of directing said predetermined change in said nucleic acid sequence, said first and second primers comprising a nucleic acid sequence substantially complementary to said double-stranded DNA so as to allow hybridization, a class IIS restriction enzyme recognition sequence and cleavage sites; (b) hybridizing said first and second primers to opposite strands of said double-stranded DNA to form a first pair of primer-templates oriented in opposite directions; (c) extending said first pair of primer-templates to create double-stranded molecules; (d) hybridizing said first and second primers at least once to said double-stranded molecules to form a second pair of primer-templates; (e) extending said second pair of primer-templates to produce double-stranded linear molecules terminating with class IIS restriction enzyme recognition sequences; and (f) restricting said double-stranded linear molecules with a class IIS restriction enzyme to form restricted linear molecules containing said change in said nucleic acid sequence. Also provided is a method of producing at least two changes located at one or more positions within a nucleic acid sequence. Synthetic primers for producing such changes are provided as well.

18 Claims, 4 Drawing Sheets

* PCR Template
  uncut plasmid
  maximum about 5 kb

* PCR:
  −denature
  −anneal primers
  −extend with
   Vent polymerase

* fill in ends with Klenow
* cut with Bsa1
* ligate
* transform
* sequence

CLASS 2S RESTRICTION ENZYMES SUITABLE FOR USE WITH EIPCR

| Enzyme | Recognition Site |
|---|---|
| Bsa1 | GGTCTCN\|NNNN |
| Bbs1 | GAAGACNN\|NNNN |
| Ear1 | CTCTTCN\|NNN |
| Bsm1 | GAATGCN\| |
| BspM1 | ACCTGCNNNN\|NNNN |
| Alw1 | GGATCNNNN\| |
| BsmA1 | GTCTCN\|NNNN |
| Bsr1 | ACTGG\|N |
| Fok1 | GGATGNNNNNNNNN\|NNNN |
| Hga1 | GACGCNNNNN\|NNNNN |
| Hph1 | GGTGANNNNNNN\|N |
| Mbo2 | GAAGANNNNNNN\|N |
| Ple1 | GAGTCNNNN\|N |
| SfaN1 | GCATCNNNNN\|NNNN |
| Mnl1 | CCTCNNNNNNN\| |

ENZYMATIC INVERSE POLYMERASE CHAIN REACTION

This application is a continuation of application Ser. No. 07/691,140, filed Apr. 26, 1991, which is now abandoned.

BACKGROUND OF THE INVENTION

This invention relates generally to the amplification of DNA sequences by polymerase chain reaction (PCR) and, more particularly, to the alteration of DNA sequences using PCR.

Recombinant DNA techniques have revolutionized molecular biology and genetics by permitting the isolation and characterization of specific DNA fragments. Of major impact has been the exponential amplification of small amounts of DNA by a technique known as the polymerase chain reaction (PCR). The sensitivity, speed and versatility of PCR makes this technique amenable to a wide variety of applications such as medical diagnostics, human genetics, forensic science and other disciplines of the biological sciences.

PCR is based on the enzymatic amplification of a DNA sequence that is flanked by two oligonucleotide primers which hybridize to opposite strands of the target sequence. The primers are oriented in opposite directions with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other primer, each cycle results in the exponential accumulation of the specific target fragment, up to several millionfold in a few hours. The method can be used with a complex template such as genomic DNA and can amplify a single-copy gene contained therein. It is also capable of amplifying a single molecule of target DNA in a complex mixture of RNAs or DNAs and can, under some conditions, produce fragments up to ten kb long. The PCR technology is the subject matter of U.S. Pat. Nos. 4,683,195, 4,800,159, 4,754,065, and 4,683,202 all of which are incorporated herein by reference.

In addition to the use of PCR for amplifying target sequences, this method has also been used to generate site-specific mutations in known sequences. Mutations are created by introducing mismatches into the oligonucleotide primers used in the PCR amplification. The oligonucleotides, with their mutant sequences, are then incorporated at both ends of the linear PCR product. In addition to their mutated sequences, the primers often contain restriction enzyme recognition sequences which are used for subcloning the mutated linear DNAs into vectors in place of the wild type sequences. Although this procedure is relatively simple to perform, its applications are limited because appropriate restriction sites are not always conveniently located for substituting the mutant sequence with the wild-type sequence. Restriction sites can be incorporated into the wild-type sequences for subcloning. However, such extraneous sequences can cause detrimental effects to the function of the gene or resulting gene product. Moreover, PCR products typically contain heterogeneous termini resulting from the addition of extra nucleotides and/or incomplete extension of the primer-templates. Such termini are extremely difficult to ligate and therefore result in a low subcloning efficiency.

Several modifications of the PCR-based site-directed mutagenesis strategies have been developed to circumvent such limitations, but they too have undesirable features. The most prominent undesirable feature exhibited by these alternative methods is a low frequency of correct mutations. For example, inverse PCR (IPCR) is a method which amplifies a circular plasmid rather than a linear molecule, Hemsley et al., Nuc. Acid. Res. 17:6545–6551 (1989), which is incorporated herein by reference. In this technique, two primers which are located back to back on opposing DNA strands of a plasmid drive the PCR reaction. The resultant PCR product, a linear DNA molecule identical in length to the starting plasmid, contains any mutations which were designed into the primers. The product is then enzymatically prepared for ligation by blunting and phosphorylating the termini. Enzymatic treatment of the termini is a necessary step for ligation due to heterogeneous termini associated with PCR products. These treatments are likely to be incomplete and cause unwanted mutations as well as result in a low ligation and transformation efficiency due to the additional required steps.

Recombinant circle PCR (RCPCR), Jones and Howard, BioTechniques 8:178–183 (1990), and recombination PCR (RPCR), Jones and Howard, BioTechniques 10:62–65 (1991), on the other hand, are two methods similar to IPCR which do not require any enzymatic treatment. In RCPCR, two separate PCR reactions, requiring a total of four primers, are needed to generate the mutated product. The separate amplification reactions are primed at different locations on the same template to generate products that when combined, denatured and cross-annealed, form double-stranded DNA with complementary single-strand ends. The complementary ends anneal to form DNA circles suitable for transformation into E. coli.

RPCR is a technique that uses PCR primers having a twelve base exact match at their 5' ends, resulting in a PCR product with homologous double-stranded termini. Transformation of the linear product into recombination-positive (recA-positive) cells produces a circular plasmid through in vivo recombination. Although this method reduces the number of steps and primers used compared to RCPCR, the transformation and recombination of linear molecules is an inefficient process resulting in a correspondingly low mutation frequency.

Thus, a need exists for a PCR-based method which allows the rapid and efficient alteration of nucleotide sequences. The present invention satisfies this need and provides related advantages as well.

SUMMARY OF THE INVENTION

The invention is directed to a method of introducing at least one predetermined change in a nucleic acid sequence of a double-strand DNA. The method includes: (a) providing a first primer and a second primer capable of directing said predetermined change in said nucleic acid sequence, said first and second primers comprising a nucleic acid sequence substantially complementary to said double-stranded DNA so as to allow hybridization, a class IIS restriction enzyme recognition sequence and cleavage sites; (b) hybridizing said first and second primers to opposite strands of said double-stranded DNA to form a first pair of primer-templates oriented in opposite directions; (c) extending said first pair of primer-templates to create double-stranded molecules; (d) hybridizing said first and second primers at least once to said double-stranded molecules to form a second pair of primer-templates; (e) extending said second pair of primer-templates to produce double-stranded linear molecules terminating with class IIS restriction enzyme recognition sequences; and (f) restricting said double-stranded linear molecules with a class IIS restriction enzyme to form restricted linear molecules containing said change in said nucleic acid sequence. Also provided is a method of producing at least two changes located at one or more positions within a nucleic acid sequence. Synthetic primers for producing such changes are provided as well.

BRIEF DESCRIPTION OF THE DRAWINGS

FIG. 2 shows the design of EIPCR primers. Line A shows a region of the PCR template (SEQ ID NO: 1) and two mutations to be made by EIPCR (indicated by small arrows). Line B shows how the primers (SEQ ID NO: 2; SEQ ID NO: 3) relate to the mutated product (line C) (SEQ ID NO: 4). This is not an actual reaction intermediate, but is a cartoon to draw when designing the primers. The primers are indicated in grey. The Bsa I recognition sequence (SEQ ID NO: 5) is underlined. Four bases are added 5' to the enzyme recognition site of each primer to ensure efficient substrate recognition by the enzyme. Line C shows the sequence of the mutated product. The grey boxes show the parts of the primer that have been incorporated into the final product. The overhangs of the two DNA ends are indicated, but the recognition sites have been cut off and are not part of the final product.

DETAILED DESCRIPTION OF THE INVENTION

The invention provides a novel method for rapid and efficient site directed mutagenesis of double-stranded linear or circular DNA. The method, termed Enzymatic Inverse Polymerase Chain Reaction (EIPCR), greatly improves the utility of previous PCR techniques enabling rapid screening of putative mutant clones.

Figure 1:
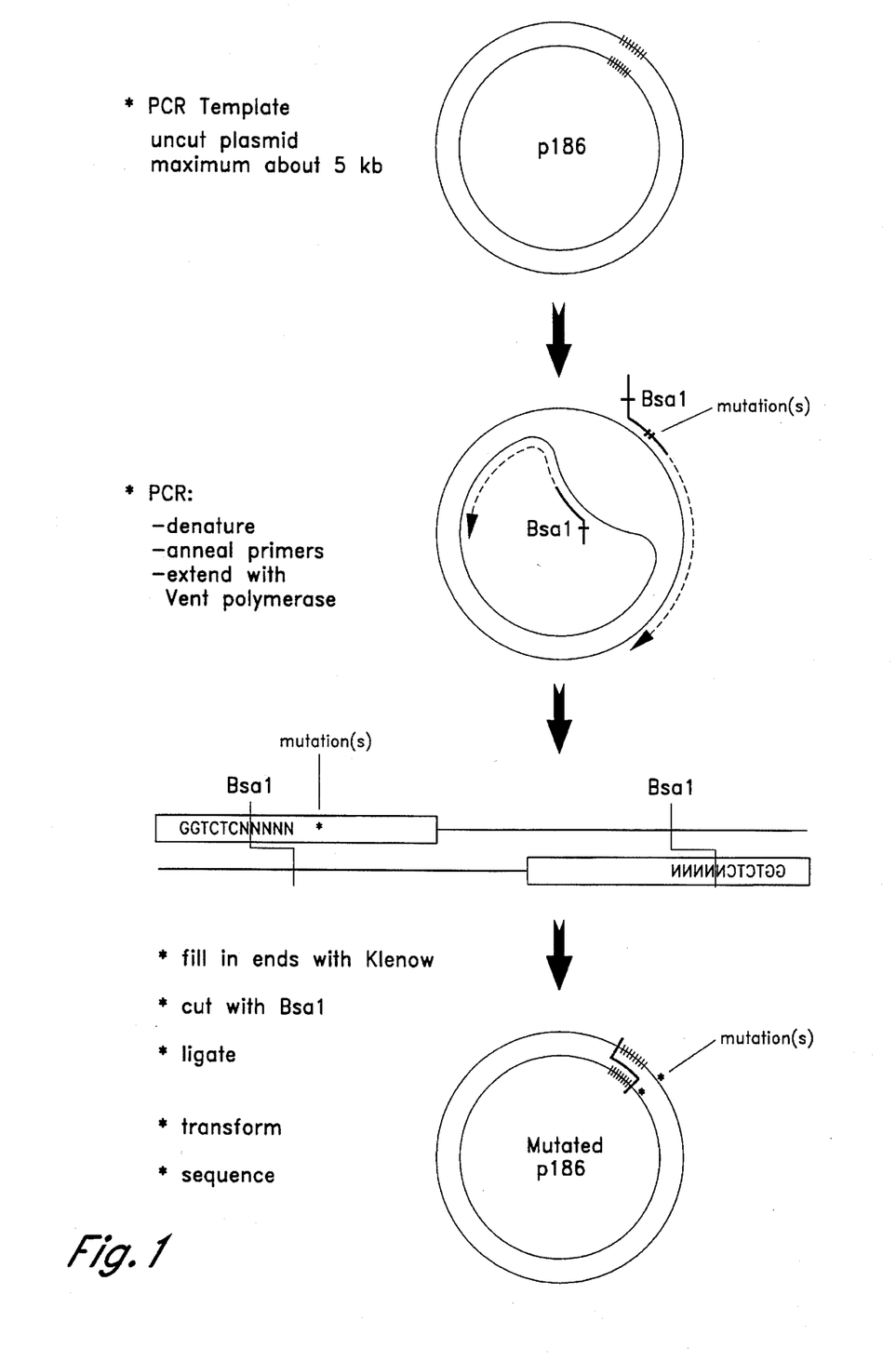
FIG. 1 is a schematic diagram outlining the steps of EIPCR.

In one embodiment, oligonucleotide primers containing the desired sequence changes are used to direct PCR synthesis of a double-stranded circular DNA template (FIG. 1). The primers are designed so that they additionally contain a class IIS restriction enzyme recognition sequence and a sequence complementary to the template for primer hybridization. The primers are hybridized to opposite strands of the circular template and direct the amplification of each strand to form linear molecules containing the desired mutations. The ends of the linear molecules are filled in with Klenow polymerase and restricted with the appropriate class IIS restriction enzyme to produce compatible overhangs for circularization and ligation.

EIPCR uses class IIS restriction enzyme recognition sequences in the mutant PCR primers. This type of recognition sequence is used because the cleavage site is separated from the recognition sequence and therefore does not introduce extraneous sequences into the final product. Restriction of the PCR products with a class IIS enzyme removes the recognition sequence and produces homogeneous termini for subsequent ligation. Class IIS recognition sequences therefore circumvent problems associated with ligating heterogeneous PCR termini since such termini will be cleaved off using a class IIS recognition enzyme. If the primers are designed with complementary cleavage sites, the resulting termini will have complementary overhangs which can be used for circularization of the linear molecules. Such complementary overhangs increase the efficiency of intramolecular ligation compared to blunt ends and result in a high percentage of correctly mutated clones. Thus, EIPCR allows efficient mutagenesis and production of homogeneous termini of any DNA template without incorporating extraneous sequences. EIPCR also allows mutagenesis at any location within a circular template independent of convenient restriction sites.

As used herein, the term "predetermined change" refers to a specific desired change within a known nucleic acid sequence. Such desired changes are commonly referred to in the art as site directed mutagenesis and include, for example, additions, substitutions and deletions of base pairs. A specific example of a base pair change is the conversion of the first A/T bp in the sequence AGCA to a G/C bp to yield the sequence GGCA. It is understood that when referring to a base pair, only one strand of a double-stranded sequence or one nucleotide of a base pair need be used to designate the referenced base pair change since one skilled in the art will know the corresponding complementary sequence or nucleotide.

As used herein, the term "class IIS restriction enzyme recognition sequence" refers to the recognition sequence of class IIS restriction enzymes. Class IIS enzymes cleave double-stranded DNA at precise distances from their recognition sequence. The recognition sequence is generally about four to six nucleotides in length and directs cleavage of the DNA downstream from the recognition site. The distance between the recognition sequence and the cleavage site as well as the resulting termini generated in the restricted product vary depending on the particular enzyme used. For example, the cleavage site can be anywhere from one to many nucleotides downstream from the 3' most nucleotide of the recognition sequence and can result in either blunt cuts or 5' and 3' staggered cuts of variable length. Such staggered cuts produce termini having single-stranded overhangs. Therefore, "complementary cleavage sites" as used herein refers to complementary nucleic acid sequences at such single-stranded overhangs. Class IIS restriction enzyme recognition sequences suitable for use in the invention can be, for example, Alw I, Bsa I, Bbs I, Bbu I, Bsm AI, Bsr I, Bsm I, BspM I, Ear I, Fok I, Hga I, Hph I, Mbo II, Ple I, SfaN I, and Mnl I. It is understood that the recognition sequence of any enzyme that utilizes this separation between the recognition sequence and the cleavage site is included within this definition.

As used herein, the term "substantially complementary" refers to a nucleotide sequence capable of specifically hybridizing to a complementary sequence under conditions known to one skilled in the art. For example, specific hybridization of short complementary sequences will occur rapidly under stringent conditions if there are no mismatches between the two sequences. If mismatches exist, specific hybridization can still occur if a lower stringency is used. Specificity of hybridization is also dependent on sequence length. For example, a longer sequence can have a greater number of mismatches with its complement than a shorter sequence without losing hybridization specificity. Such parameters are well known and one skilled in the art will know, or can determine, what sequences are substantially complementary to allow specific hybridization.

As used herein, the term "a primer capable of directing" when used in reference to nucleic acid sequence changes refers to a primer having a mismatched base pair or base pairs within its sequence compared to the template sequence. Such mismatches correspond to the mutant sequences to be incorporated into the template and can include, for example, additional base pairs, deleted base pairs or substitute base pairs. It is understood that either one or both primers used for the PCR synthesis can have such mismatches so long as together they incorporate the desired mutations into the wild-type sequence.

Thus, the invention provides methods of introducing at least one predetermined change in a nucleic acid sequence of a double-stranded DNA. Such methods include: (a) providing a first primer and a second primer capable of directing said predetermined change in said nucleic acid sequence, said first and second primers comprising a nucleic acid sequence substantially complementary to said double-stranded DNA so as to allow hybridization, a class IIS restriction enzyme recognition sequence and cleavage sites; (b) hybridizing said first and second primers to opposite strands of said double-stranded DNA to form a first pair of primer-templates oriented in opposite directions; (c) extending said first pair of primer-templates to create double-stranded molecules; (d) hybridizing said first and second primers at least once to said double-stranded molecules to form a second pair of primer-templates; (e) extending said second pair of primer-templates to produce double-stranded linear molecules terminating with class IIS restriction enzyme recognition sequences; and (f) restricting said double-stranded linear molecules with a class IIS restriction enzyme to form restricted linear molecules containing said change in said nucleic acid sequence.

Enzymatic Inverse Polymerase Chain Reaction (EIPCR) is a PCR-based method for performing site-directed mutagenesis. Mutations are introduced into a DNA by first hybridizing primers which contain the desired mutations to the DNA, referred to herein as mutant primers. The resulting primer-templates are enzymatically extended with a polymerase to yield an intermediate product. Repriming of the intermediates and polymerase extension will yield the final mutant product. Cohesive termini can be subsequently generated for circularization of the linear products by intramolecular ligation.

The invention is described with particular reference to introducing a predetermined change into a circular template and recircularizing of the product to generate mutant copies of the starting template. However, one skilled in the art can use the teachings and methods described herein to similarly generate mutations in linear templates. The primers designed for use on linear templates are similar to those used for circular templates. Appropriate modifications of primers for use on linear templates are known to one skilled in the art and will be determined by the intended use of the final mutant product. For example, when generating circular products, either from a linear or circular starting template, it is beneficial to use primers containing complementary cleavage sites downstream from the class IIS recognition sequence. Such complementary sites greatly increase the efficiency of intramolecular ligation. With linear molecules, on the other hand, while it is beneficial in some cases for the primers to contain class IIS recognition sequences which produce single-stranded overhangs at their cleavage sites, such cleavage sites need not be complementary. For example, if the product is a linear molecule for subcloning into a vector, cleavage sites which are not complementary can be used for directional cloning of the product. Additionally, a blunt cleavage site can be used to eliminate sequence requirements for subcloning. Thus, depending on the desired product, the cleavage sites within the primers can be complementary or non-complementary.

EIPCR primers are synthesized having three basic sequence components. These sequences are used for generating mutations and for enabling efficient formation of circular products without introducing unwanted sequences or requiring the use of template restriction sites. The first sequence component of the primers is the region which directs the predetermined changes. This region contains the desired mutations which are to be introduced into the template. The length and sequence of this region will depend on the number and locations of incorporated mutations. For example, if multiple and adjacent mutations are desired, then the primer will not contain any nucleotides within this region identical to the wild-type sequence. However, if the mutations are not located at adjacent positions, then the nucleotides in between such mutations will be identical to the wild-type sequence and capable of hybridizing to the appropriate complementary strand. Thus, the region can be from one to many nucleotides in length so long as it contains the desired mismatches with the wild-type sequence.

Figure 2:
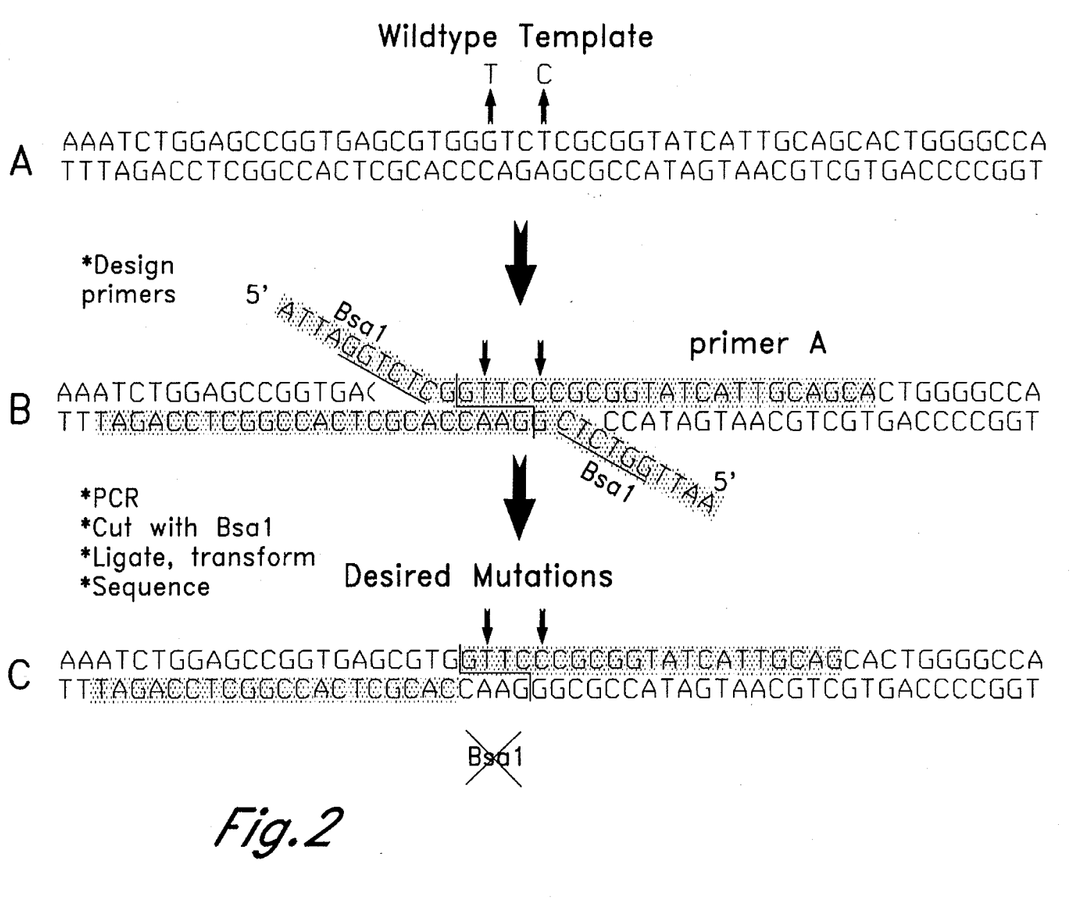

It is only necessary for one of the primers to contain the desired mutations but a higher efficiency of correct mutations can be obtained if both primers contain the desired mutations on each complementary strand. A strategy for designing EIPCR primers is outlined in FIG. 2. This strategy shows an example of a pair of primers which can be used for mutagenesis at two nonadjacent locations. One skilled in the art can use this strategy and the teachings described herein to design and use primers that incorporate essentially any desired mutation into a double-stranded DNA. The template containing the wild-type sequence is shown in FIG. 2A (SEQ ID NO: 1). Also shown are the desired nucleotide substitutions (arrows). The actual primers are depicted in FIG. 2B as the shaded sequence (SEQ ID NO: 2; SEQ ID NO: 3). The region of each primer containing the desired substitutions is complementary and corresponds to the opposite strand at the same location within the template (FIG. 2C) (SEQ ID NO: 4). For primers A (SEQ ID NO: 2) and B (SEQ ID NO: 3) in FIG. 2B, the mutant region would consist of the sequence GTTCC and its complement, respectively.

The second sequence component of EIPCR primers is the region containing the class IIS restriction enzyme recognition sequence. The location of the recognition sequence is 5' to the mutant region and thus is incorporated at the termini of any extension products. Since recognition sequences are located at the ends of linear extension products, they can also contain additional 5' sequences to facilitate recognition and cleavage by a class IIS enzyme. For example, the primers in FIG. 2B (SEQ ID NO: 2; SEQ ID NO: 3) contain four additional nucleotides 5' to the Bsa I recognition sequence (SEQ ID NO: 5).

Other sequences included within the recognition sequence component of EIPCR primers are the nucleotides between the recognition sequence and the cleavage site. The number of nucleotides will correspond to the distance between these two sites and therefore will vary for different enzymes. For example, the primers of FIG. 2 contain a Bsa I recognition sequence which is cleaved by Bsa I on opposite (SEQ ID NO: 5) strands one and five nucleotides, respectively, 3' to the recognition sequence, leaving a four nucleotide single-strand overhang. Generally, such overhang sequences within the primers are completely complementary to each other but can include limited mismatches. Primers are synthesized with "spacer" nucleotides placed 5' to the first cleavage site to prevent incorporation of sequences other than the desired mutations into the final product. The number of spacer nucleotides corresponds to the distance between the particular class IIS recognition sequence used and its cleavage site. The sequence of such spacer nucleotides can, for example, correspond to wild-type or non-wild-type sequences or to predetermined mutations. For generating just a few point mutations, it is beneficial to match these nucleotides to the wild-type sequence to increase the hybridization stability of the adjacent mutant primer region.

Types of restriction enzyme recognition sequences to be used in the invention are those recognized by class IIS enzymes. These enzymes recognize the DNA through a sequence specific interaction and cleave it at a discrete distance downstream from the recognition sequence. The ability to cleave such sequences downstream provides a useful means to remove heterogeneous ends and to produce complementary termini for circularization while at the same time removing the recognition sequence from the final product. Specific examples of class IIS recognition sequences have been listed previously and are also listed in FIG. 3 along with their nucleotide sequences and cleavage sites (SEQ ID NOS: 5 through 20). Although recognition sequences having complementary cleavage sites associated with them are preferred, those which have blunt ended cleavage sites can also be used in the invention.

The third sequence component of EIPCR primers is the region to be hybridized to the template DNA. This region must be sufficient in length and sequence to allow specific hybridization to the template. The hybridized portion of the primers must also form a stable primer-template which can be used as a substrate for polymerase extension. It is typically found 3' to the mutant primer region and its sequence is determined with respect to the location of the desired mutations. For example, for the primers shown in FIG. 2 (SEQ ID NO: 2; SEQ ID NO: 3), the hybridization region is twenty nucleotides in length and found 3' to the mutant region. However, the hybridization region can also be 5' to the mutant region. For this orientation, the mutant region must form a stable primer-template which can be used as a substrate for polymerase extension. Longer or shorter hybridization sequences can be used in this region so long as they are appropriately located with respect to the mutant region and also specifically hybridize to the template molecule. One skilled in the art knows or can readily determine the specificity of such hybridization regions for use in EIPCR primers.

Thus, the invention also provides a synthetic primer for introducing at least one predetermined change in a nucleic acid sequence of a double-stranded circular DNA. The primer includes: (a) a class IIS restriction enzyme recognition sequence; (b) said predetermined change in said nucleic acid sequence; and (c) a nucleic acid sequence substantially complementary to said double-stranded DNA. The preferred orientation of the above regions (a) through (c) is in a 5' to 3' direction.

The above described primers can be, for example, hybridized to a double-stranded circular DNA which has first been denatured. Denaturation can be performed, for example, using heat or an alkaline solution. Other methods known to one skilled in the art can also be used.

Hybridization of the primers occurs on opposite strands of the circular template and in a location where the single-stranded overhangs of each primer's complementary cleavage site can be joined together by restriction and ligation. Preferably, such joining should occur so that the wild-type sequence is reformed except for the incorporation of the desired mutations. One way to ensure proper sequence reconstruction is to design the primers such that their complementary cleavage sites overlap and are either identical to the template sequence or contain some or all of the desired mutations. Such primers, once hybridized to a double-stranded circular DNA, form primer-templates and can be extended with a polymerase. The first extension reactions of circular templates result in the synthesis of double-stranded circular products which can be concatenated. Depending on the extent of polymerization, the concatemers can be either partially or completely double-stranded. It is necessary for polymerization to proceed sufficiently far to allow subsequent primer hybridization for a second extension reaction. Smaller circular DNAs result in a greater number of completely double-stranded products and also require shorter extension times compared to much larger circles. Small circular DNAs of less than 1.0 kb are known in the art. Such vectors are beneficial to use in the invention since they can accommodate large inserts (3 to 5 kb) and still be comparable in size to most standard cloning vectors. The plasmid pVX is a specific example of a 902 bp vector, Seed, B., Nuc. Acids Res. 11:2477–2444 (1983), which is incorporated herein by reference. Such vectors can be further modified by the addition of, for example, promoters, terminators and the like to achieve the desired end. Complete extension of a circular DNA of about 5.0 kb can be achieved using the conditions described herein; however, alternative conditions used by those skilled in the art to achieve complete extension of larger circular DNAs can also be used to practice the invention. For linear templates, on the other hand, the first extension reaction produces a double-stranded linear molecule known in the art as the long product.

After one extension reaction, the double-stranded products, whether they exist as circular or linear molecules, have incorporated at one of their ends the EIPCR primer with its associated class IIS restriction enzyme recognition sequence and the desired mutations. These double-stranded molecules can be used for a second cycle of hybridization and extension to produce double-stranded linear molecules which terminate at both ends with EIPCR primers. Further cycles will result in the exponential amplification of template sequence located between each primer on the circular DNA. Thus, the location of the hybridized primers defines the termini of template sequences to be amplified.

Polymerases which can be used for the extension reaction include all of the known DNA polymerases. However, if multiple cycles of hybridization and extension are to be performed, such as required for PCR amplification, then preferably a thermostable polymerase is used. Thermostable polymerases include, for example, Taq polymerase and Vent polymerase. Vent polymerase advantageously exhibits a higher fidelity than Taq due to its 3' to 5' proofreading capability.

Following synthesis of the linear molecules, the products are restricted with the appropriate class IIS restriction enzyme to remove the class IIS recognition sequence and heterogeneous termini and to create cohesive termini used for circularization. The resulting termini correspond to the single-strand overhangs produced after restriction of each primer's complementary cleavage site. To facilitate proper recognition and cleavage, the linear products can be pre-pre-treated with a polymerase, such as Klenow, under conditions which create blunt ends. This procedure will fill in any uncompleted product ends produced during amplification and allows efficient restriction of essentially all of the products. After restriction, the cohesive termini can be joined to recircularize the linear molecule. Covalently closed circles can subsequently be formed in vitro with a ligase. Alternatively, in vivo ligation can be accomplished by introducing the circularized products into a compatible host by transformation or electroporation, for example.

Transformation or electroporation of the circularized products can additionally be used for the propagation and manipulation of mutant products. Such techniques and their uses are known to one skilled in the art and are described, for example, in Sambrook et al., Molecular Cloning: A Laboratory Manual, Cold Spring Harbor, Cold Spring Harbor, N.Y. (1989), or in Ausubel et al., Current Protocols in Molecular Biology, John Wiley and Sons, New York, N.Y. (1989), both of which are incorporated herein by reference. Propagation and manipulation procedures do not have to be performed at the end of all EIPCR reactions. The need will determine whether such procedures are necessary. For example, transformation and DNA preparation can be eliminated if two consecutive EIPCR reactions are to be performed where the product of the first reaction is used as the template for the second reaction. All that is necessary is that the first reaction products are circularized and ligated prior to hybridization with the second reaction primers. Additionally, primers for EIPCR do not need to be purified. EIPCR is not sensitive to the presence of primers of incomplete length because the non-uniform DNA ends are removed by restriction of the class IIS recognition sequence.

The invention further provides methods of producing at least two changes located at one or more positions within a nucleic acid sequence of a double-stranded circular DNA. The methods include: (a) providing a first population of primers and a second population of primers capable of directing said changes in said nucleic acid sequence, said first and second populations of primers comprising a nucleic acid sequence substantially complementary to said double-stranded DNA so as to allow hybridization, a class IIS restriction enzyme recognition sequence, and cleavage sites; (b) hybridizing said first and second populations of primers to opposite strands of said double-stranded DNA to form a first pair of primer-template populations orientated in opposite directions; (c) extending said first pair of primer-template populations to create a population of double-stranded molecules; (d) hybridizing said first and second populations of primers at least once to said population of double-stranded molecules to form a second pair of primer-template populations; (e) extending said second pair of primer-template populations to produce a population of double-stranded linear molecules terminating with class IIS restriction enzyme recognition sequences; and (f) restricting said population of double-stranded linear molecules with a class IIS restriction enzyme to form a population of restricted linear molecules containing said changes within said nucleic acid sequence. Also provided is a population of synthetic primers for producing at least two changes located at one or more positions within a nucleic acid sequence of a double-stranded circular DNA comprising:

(a) a class IIS restriction enzyme recognition sequence;

(b) said changes within said nucleic acid sequence; and (c) a nucleic acid sequence substantially complementary to said double-stranded circular DNA.

The method for producing at least two changes located at one or more positions is similar to that described above for site-directed mutagenesis except that the primers can have more than one nucleotide change at a desired position. For example, if it is desirable to produce mutations incorporating from two to four different mutant nucleotides at a particular position, then a population of primers should be synthesized such that all mutant nucleotides are represented within the entire population. Each individual primer within the population will contain only a single mutant nucleotide. The proportion of primers containing identical mutant nucleotides will determine the expected frequency of that mutation being correctly incorporated into the final product. For example, if only two mutant nucleotides are desired and each one is equally represented within the primer population, then 50% of the products should contain one of the mutations and 50% should contain the other mutation. If more than two mutations are desired at a particular position or at more than one position, then primer populations should be synthesized which contain individual primers having each of the desired mutations. Primer populations can also be synthesized which direct single mutations at one position and multiple mutations at another position by incorporating one or more mutant nucleotides at the appropriate position.

The design and use of such primers is identical to that previously described for introducing at least one predetermined change into a double-stranded circular DNA. The only difference is that instead of hybridizing a first primer and a second primer to form a pair of primer-templates, hybridization is with a first population of primers and a second population of primers to form a pair of primer-template populations. Each primer-template within the population can include, for example, one of the desired mutant sequences to be incorporated into the resultant products. Amplification of the primer-template population will produce a population of linear products containing all desired mutations. The products can be restricted, circularized and screened for individual mutant clones. Screening can be performed, for example, by sequencing or expression. If applicable, expression screening offers the advantage of screening a large number of clones in a relatively short period of time.

The methods and primers described herein can be used to create essentially any desired change in a nucleic acid sequence. Templates can be linear or circular and result in products containing only the desired changes since class IIS recognition sequences allow the removal of extraneous and unwanted sequences. Product termini which are homogeneous in nature are also produced using the class IIS recognition sequences. Use of circular templates allows the incorporation of mutations at any desired location along the template with subsequent recircularization of the mutant products. Thus, additions, deletions and substitutions of single base pairs, multiple base pairs, gene segments and whole genes can rapidly and efficiently be produced using EIPCR. A specific use of EIPCR would be in the mutagenesis of antibodies or antibody domains. Mutagenesis of antibody complementary determining regions (CDR), for example, can be performed using EIPCR for the rapid generation of antibodies exhibiting altered binding specificities. Likewise, EIPCR can also be used for producing chimeric and/or humanized antibodies having desired immunogenic properties.

The efficiency of incorporating correct mutations into the product using EIPCR can be, for example, greater than about 95%, preferably about 98 to 99%, more preferably about 100%. This efficiency is routinely obtained when using about 0.5 to 2.0 ng of template in a 25 cycle PCR reaction. However, it should be understood that the efficiency directly correlates with the number of amplification cycles and inversely with the amount of template used. For example, the more amplification cycles which are performed, the greater the amount of mutant product present and therefore a larger fraction of mutant sequences will be present within the total sequence population. Conversely, if a large amount of template is used, more amplification cycles are required, compared to using a smaller amount of template, to achieve the same fraction of mutant sequences within the total sequence population. One skilled in the art knows such parameters and can adjust the number of cycles and amount of template required to achieve the required efficiency.

The following examples are intended to illustrate but not limit the invention.

EXAMPLE I

This example shows the use of EIPCR for site-directed mutagenesis of two bases located on a 2.6 kb pUC-based plasmid (designated p186).

Figure 3:
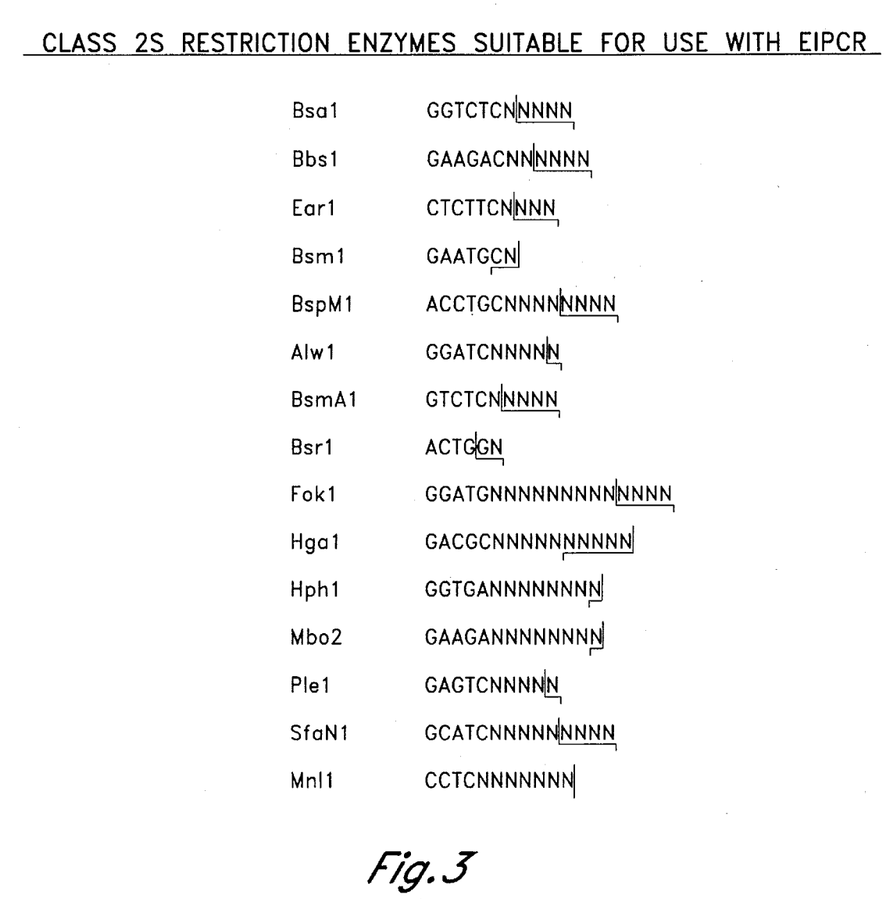
FIG. 3 is a list of class IIS restriction enzymes and the nucleotide sequence of their recognition sequences (SEQ ID NOS: 5 through 20).

The design of the primers and their relationship to the template and to the final mutant sequence is shown in FIG. 2. The 3' end of the primer is an exact match of 20 bases. The 5' ends of the primers comprise the enzyme recognition site and the enzyme cut site, which was designed to form complementary overhangs. Four additional bases were added 5' to the enzyme recognition site to facilitate recognition and digestion of the PCR product by the enzyme. Two complementary mutations were designed into each of the primers. Bsa 1 was the enzyme used to make the overhangs (FIG. 3).

PCR reactions were performed in 100 μl volumes containing 0.2–1.0 uM of each unpurified primer, 0.5 ng uncut p186 template plasmid DNA, 1x Vent buffer, 200 uM of each dNTP, 2.5 units Vent polymerase (New England Biolabs, Beverly, Mass.). Thermal cycling was performed on a Perkin-Elmer-Cetus PCR machine (Emeryville, Calif.) with the following parameters: 94° C./3 minutes for 1 cycle; 94° C./1 minute, 50° C./1 minute, 72° C./3–4 minutes for 3 cycles; 94° C./1 minute, 55° C./1 minute, 72° C./3–4 minutes, with autoextension at 4–6 sec/cycle for 25 cycles; followed by one 10 minute cycle at 72° C.

To blunt the ends of the PCR product, the entire reaction mix was supplemented with 8 ul of 10 mM of dNTP mixture (2.5 mM each) and 20 units of Klenow fragment (Gibco-BRL, Gaithersburg, Md.) incubated at 37° C. for 30 minutes. The reaction was then extracted with an equal volume of phenol/chloroform (1:1), ethanol-precipitated, and the pellet was washed and dried. The blunt end product was then restriction digested with Bsa I (New England Biolabs, Beverly, Mass.) as recommended by the manufacturer. The digested DNA was extracted with an equal volume of phenol/chloroform, ethanol-precipitated, as described above, and ligated with 20 units T4 DNA ligase (Gibco-BRL) for one hour at room temperature. Gel-purification of the digested DNA before ligation was not necessary. After ligation, the DNA was transformed into competent DH10B cells recommended by the manufacturer (Gibco-BRL).

Approximately 400 colonies were obtained from a transformation using 10 ng of DNA into 30 ul of frozen competent cells. The transformation efficiency was $4\times10^4$ cfu/ug of DNA. Seven colonies were randomly picked and plasmid DNA was prepared for restriction digests. No differences in restriction pattern were seen. The mutated areas of the plasmids of these seven colonies were sequenced. Double-stranded dideoxy sequencing was performed on a Dupont Genesis 2000 automated sequencer using the Dupont Genesis 2000 sequencing kit. The sequences of all seven plasmids contained the desired mutation.

EXAMPLE II

This example shows the use of EIPCR for constructing large libraries of protein mutants.

The binding site of an antibody, called the Fv fragment, normally consists of a heavy chain and a light chain, each about 110 amino acids long. Using molecular modelling tools, several groups have constructed single chain Fv fragments (scFv) in which the c-terminus of one chain is connected by a 10–15 amino acid linker to the n-terminus of the other chain (Huston, Bird, Glockshuber). The single chain construct was shown to be much more stable than the two chain Fv.

Figure 4:
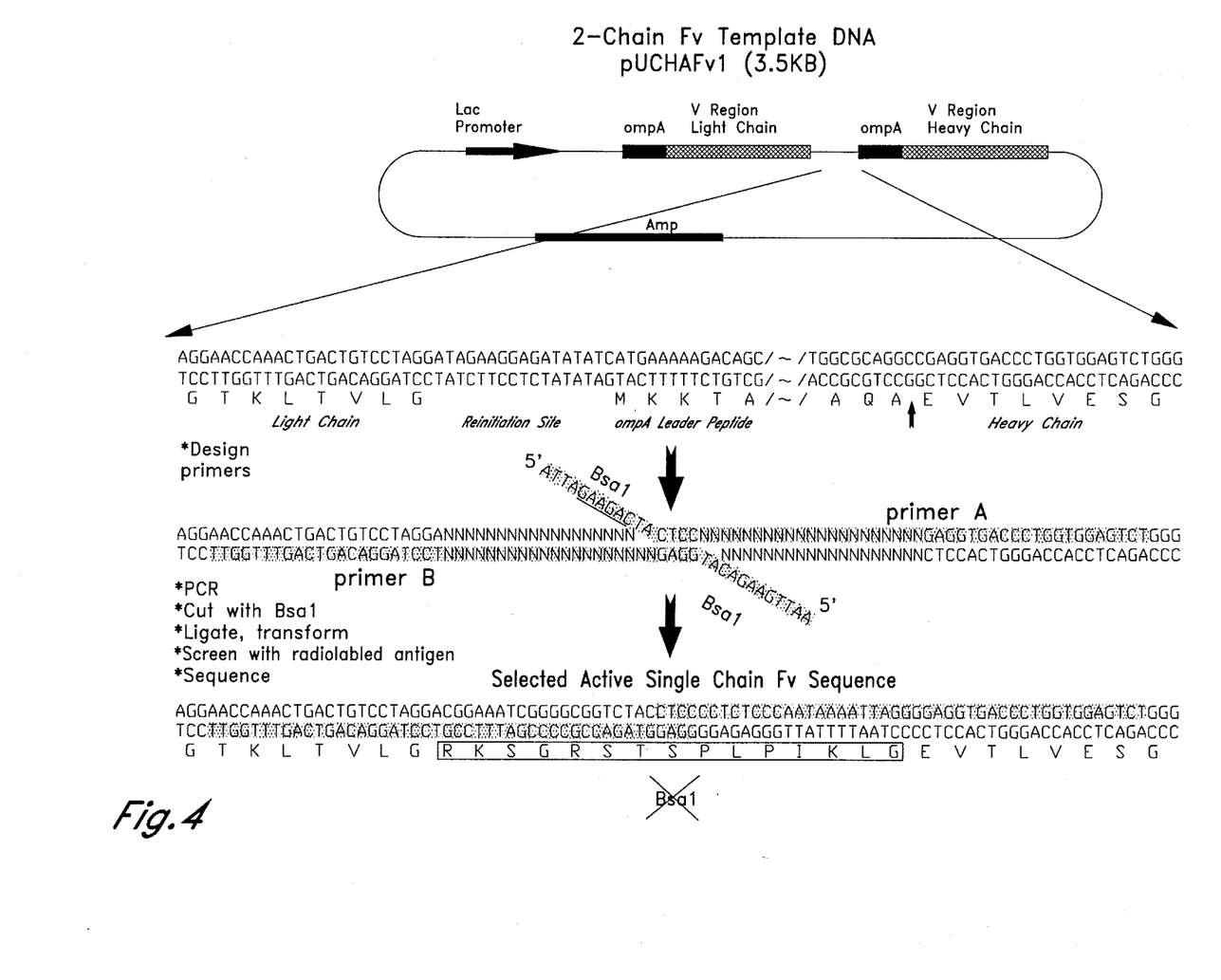
FIG. 4 is a schematic diagram showing the use of EIPCR technology for generating single chain antibodies. Line A shows the template region (SEQ ID NO: 21) to be mutagenized to create a linker between heavy and light chain encoding sequences. Line B shows the EIPCR primer design (SEQ ID NO: 22; SEQ ID NO: 23) and line C shows the nucleotide (SEQ ID NO: 24) and amino acid (SEQ ID NO: 25) sequence of a selected, active single chain antibody sequence.

To eliminate the need for molecular modelling, EIPCR was used to make a large library of different linkers and screen for a scFv clone that is not only active but also expressed at a high level. An antibody was chosen that binds a radioactive Indium chelate, Reardan et al., Nature 316:265–267 (1985), which is incorporated herein by reference. A 3.5 kb pUC-derived plasmid was constructed in which both Fv chains are attached to ompA leader peptides and driven by a Lac promoter (FIG. 4). This plasmid was used as the template for EIPCR in which the DNA between the c-terminus of the first chain and the n-terminus of the mature second chain was replaced by a random mixture of bases, encoding a library of random linkers. The design of the primers is shown in FIG. 4B in the shaded region where N represents an equal proportion of all four nucleotides at the position within the primer population.

Synthesis of the two primer populations used to construct the library was performed on a Milligen/Biosearch 8700 DNA synthesizer. The mixed base positions were synthesized using a 1:1:1:1 mixture of each of the four bases in the U reservoir. The oligonucleotides were made trityl-on and were purified with Nensorb Prep nucleic acid purification columns (NENDupont, Boston, Mass.) as described by the manufacturer.

PCR reactions were performed in 100 μl volumes containing 0.5 uM of each unpurified primer, 0.5 ng pUCHAFv1 template plasmid DNA, digested with Sty I, 1x Taq buffer, 200 uM of each dNTP, 1 ul Taq polymerase (Perkin-Elmer-Cetus). Thermal cycling was performed on a Perkin-Elmer-Cetus PCR machine with the following parameters: 94° C./3 minutes for 1 cycle; 94° C./1 minute, 50° C./1 minute, 72° C./2 minutes for 3 cycles; 94° C./1 minute, 55° C./1 minute, 72° C./2 minutes, with autoextension at 4 sec/cycle for 25 cycles; followed by one 10 minute cycle at 72° C.

The product of the 100 ul PCR was extracted with an equal volume of phenol/chloroform (1:1), ethanol-precipitated, and the pellet was resuspended in 20 ul KKL buffer (50 mM Tris-HCl pH 7.6, 10 mM MgCl2, 5 Mm DTT; suitable for Klenow, Kinase and Ligase) containing 200 μM dNTPs, 10 units DNA Polymerase Klenow fragment and 10 units T4 DNA Kinase and incubated at 37° C. for 30 minutes. Then 2 ul 10 Mm ATP and 10 units T4 DNA ligase were added, and the reaction was continued for 2 hours at room temperature. The enzymes were then inactivated by heating at 65° C. for 10 minutes. The polymerized DNA was then digested with Bbs I (NEB) which cuts off the ends of the PCR fragment, inside the oligos. It was found that Bbs I digestion was inefficient with only four bp 5' to the recognition sequence. To create a longer 5' extension and improve efficiency, the DNA was ligated before digestion. Alternatively, primers could have been synthesized with longer 5' extensions. The digested DNA was then extracted with phenol/chloroform, ethanol precipitated, and resuspended in 20 ul 1x NEB ligation buffer, containing 1 mM ATP and 10 units T4 DNA ligase and the reaction was incubated for 2 hours at room temperature.

One microliter amounts of the ligation reaction were electroporated into 20 ul of DH10B Electromax cells (Gibco-BRL, Gaithersburg, Md.) to produce a library of scFv constructs. The Gibco-BRL electroporator and voltage booster was used as recommended by the manufacturer. Cells were plated at 3,000 cfu/plate on plates containing 0.05 mM IPTG, to induce Fv expression.

For screening, the labelled chelate was prepared by incubating 10 ul of 0.075 mM Eotube chelate with 50 uCi of buffered $^{111}$Indium Chloride in a metal free tube. Colony lifts of the petri plates containing the protein library were prepared using BA83 nitrocellulose filters (Schleicher and Schuell, Keene, NH). The filters were blocked by incubation in Blotto (7% non-fat milk in PBS) for 10 minutes, washed with PBS, followed by incubation in Blotto containing 10 uCi of $^{111}$Indium Chloride per filter for 1 hour at room temperature. The filters were then washed repeatedly with PBS for a total of 15 minutes, dried and exposed to Kodak X-omat AR autoradiography film for several hours.

The quality of the protein library was determined by DNA sequencing of the linker of several unscreened clones. Sequencing was performed as described in Example I. The composition of the mixed site residues was 19% G, 31% A, 25% T, 25% C (n=119).

The size of the library was determined by plating. In a typical electroporation, 30,000 cfu's were obtained from electroporation of 1 ul of ligation mixture into 20 ul of cells. The ligation contained 0.1 ug of DNA in 20 ul. The library size was about $6 \times 10^5$ recombinants and the electroporation efficiency was $6 \times 10^6$ cfu/ug. Approximately 30,000 clones were screened, and about 60 colonies gave a range of signals on the primary screen (0.02%). Those with the strongest signal were colony purified and the DNA sequence of the linker was determined. The sequences of one linker from a selected scFv is shown in FIG. 4C.

Although the invention has been described with reference to the presently-preferred embodiment, it should be understood that various modifications can be made by those skilled in the art without departing from the invention. Accordingly, the invention is limited only by the following claims.

---

I claim:

1. A method of introducing at least one predetermined change in a circular double-stranded DNA sequence comprising:

(a) providing a first primer and a second primer wherein said first and second primers each comprise in a 5' to 3' orientation a class IIS restriction enzyme recognition sequence, a class IIS restriction enzyme cleavage site associated with said class IIS restriction enzyme recognition sequence, said predetermined change to be incorporated into said double-stranded circular DNA sequence, and a sequence substantially complementary to said double-stranded DNA;

(b) hybridizing said first and second primers to opposite strands within the same region of said double stranded DNA sequence in the same reaction vessel;

(c) performing at least one cycle of a polymerase chain reaction to produce double-stranded linear molecules terminating with said class IIS restriction enzyme recognition sequence and including said class IIS restriction enzyme cleavage site and said predetermined change;

(d) cleaving said double-stranded linear molecules with at least one class IIS restriction enzyme at said class IIS restriction enzyme cleavage sites to produce overhanging termini that are complementary to one other; and (e) ligating said overhanging termini to recircularize said double-stranded linear molecules containing said predetermined change.

2. The method of claim 1, wherein said cleaved double-stranded linear molecules produced in step (d) contain only said predetermined change incorporated into the primers of step (a), and the efficiency of introducing said predetermined change in said circular double-stranded DNA sequence is greater than about 95%.

3. The method of claim 1, wherein said class IIS restriction enzyme recognition sequence is selected from the group consisting of those recognized by the restriction enzymes Bsa I, Bbs I, Ear I, Bsm I, BspM I, Alw I, Bbu I, BsmA I, Bsr I, Fok I, Hga I, Hph I, Mbo II, Ple I and SfaN I.

4. The method of claim 1, wherein said predetermined change in said DNA sequence is located immediately adjacent to said cleavage site of said double-stranded linear molecules.

5. The method of claim 1, wherein said predetermined change in said DNA sequence is located between said cleavage site of said double-stranded linear molecules and said sequence substantially complementary to said double-stranded circular DNA.

6. The method of claim 1, further comprising step (f) introducing said recircularized double-stranded molecules of step (e) into a host cell.

7. The method of claim 6, wherein said introducing step is performed by transformation or electroporation.

8. In a method of introducing at least one predetermined change in a circular double-stranded DNA sequence by polymerase chain reaction the improvement comprising, using primers comprising in a 5' to 3' orientation: (a) a class IIS restriction enzyme recognition sequence, (b) a class IIS restriction enzyme cleavage site associated with said class IIS restriction enzyme recognition sequence, (c) said predetermined change to be incorporated into said double-stranded circular DNA sequence and (d) a sequence substantially complementary to said double-stranded DNA, wherein the use of said primers allows restriction endonuclease cleavage of the PCR product with a class IIS enzyme for the removal of heterogenous termini.

9. A method of introducing at least two changes located at one or more positions within a circular double-stranded DNA sequence comprising:

(a) providing a first primer and a second primer population wherein said first and second primer populations each comprise in a 5' to 3' orientation a class IIS restriction enzyme recognition sequence, a class IIS restriction enzyme cleavage site associated with said class IIS restriction enzyme recognition sequence, said changes to be incorporated into said double-stranded circular DNA sequence, and a sequence substantially complementary to said double-stranded DNA;

(b) hybridizing said first and second primer populations to opposite strands of the same region of said double-stranded DNA sequence in the same reaction vessel;

(c) performing at least one cycle of a polymerase chain reaction to produce a population of double-stranded linear molecules terminating with said class IIS restriction enzyme recognition sequence and including said class IIS restriction enzyme cleavage site and said changes in said double-stranded DNA sequence;

(d) cleaving said double-stranded linear molecules with at least one class IIS restriction enzyme at said class IIS restriction enzyme cleavage sites to produce overhanging termini that are complementary to one other; and (e) ligating said overhanging termini to recircularize said double-stranded linear molecules containing said changes located at one or more positions within said nucleic acid sequence.

10. The method of claim 9, wherein said cleaved linear molecules produced in step (d) contain only said changes located at one or more positions within said double-stranded DNA sequence, and the efficiency of introducing said changes within said circular double-stranded DNA sequence is greater than about 95%.

11. The method of claim 9, wherein said class IIS restriction enzyme recognition sequence is selected from the group consisting of those recognized by the restriction enzymes Bsa I, Bbs I, Ear I, Bsm I, BspM I, Alw I, Bbu I, BsmA I, Bsr I, Fok I, Hga I, Hph I, Mbo II, Ple I and SfaN I.

12. The method of claim 9, wherein said changes within said nucleic acid sequence are located within said cleavage site of said double-stranded linear molecules.

13. The method of claim 9, wherein said changes within said nucleic acid sequence are located between said cleavage site of said population of double-stranded linear molecules and said nucleic acid sequence substantially complementary to said double-stranded circular DNA.

14. The method of claim 9, further comprising step (f) introducing said population of double-stranded molecules of step (e) into a host cell.

15. The method of claim 14, wherein said introducing step is performed by transformation or electroporation.

16. In a method of producing at least two changes located at one or more positions in a circular double-stranded DNA sequence by polymerase chain reaction the improvement comprising, using primers comprising in a 5' to 3' orientation: (a) a class IIS restriction enzyme recognition sequence, (b) a class IIS restriction enzyme cleavage site associated with said class IIS restriction enzyme recognition sequence, (c) said predetermined change to be incorporated into said double-stranded circular DNA sequence and (d) a sequence substantially complementary to said double-stranded DNA wherein the use of said primers allows restriction endonuclease cleavage of PCR products with a class IIS enzyme for the removal of heterogenous termini.

17. A synthetic primer for introducing at least one predetermined change in a DNA sequence of a double-stranded circular DNA comprising in a 5' to 3; orientation:

(a) a class IIS restriction enzyme recognition sequence;

(b) a class IIS restriction enzyme cleavage site associated with said class IIS restriction enzyme recognition sequence;

(c) said predetermined change in said DNA sequence; and (d) a DNA sequence substantially complementary to said double-stranded circular DNA, wherein the DNA sequence immediately adjacent to said class IIS restriction enzyme cleavage site within said synthetic primer is not complementary to the DNA sequence of the region of said double-stranded circular DNA incorporating said predetermined change.

18. A population of synthetic primers for producing at least two changes located at one or more positions within a DNA sequence of a double-stranded circular DNA comprising in a 5' to 3; orientation:
  (a) a class IIS restriction enzyme recognition sequence;
  (b) a class IIS restriction enzyme cleavage site associated with said class IIS restriction enzyme recognition sequence;
  (c) said changes in said DNA sequence; and
  (d) a DNA sequence substantially complementary to said double-stranded circular DNA, wherein the DNA sequence immediately adjacent to said class IIS restriction enzyme cleavage site within said synthetic primer is not complementary to the DNA sequence of the region of said double-stranded circular DNA incorporating said predetermined change, and wherein said population of primers includes more than one nucleotide change at one or more positions.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: circular     ( i i ) MOLECULE TYPE: cDNA     ( x i ) SEQUENCE DESCRIPTION: SEQ ID NO:1:

```
AAATCTGGAG  CCGGTGAGCG  TGGGTCTCGC  GGTATCATTG  CAGCACTGGG  GCCA           54
```

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

```
ATTAGGTCTC  GGTTCCCGCG  GTATCATTGC  AGCACT                                 36
```

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

```
AATTGGTCTC  GGAACCACGC  TCACCGGCTC  CAGAT                                  35
```

( 2 ) INFORMATION FOR SEQ ID NO:4:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: circular     ( i i ) MOLECULE TYPE: cDNA     ( x i ) SEQUENCE DESCRIPTION: SEQ ID NO:4:

AAATCTGGAG CCGGTGAGCG TGGTTCCCGC GGTATCATTG CAGCACTGGG GCCA     54

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

GGTCTCNNNN N     11

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

GAAGACNNNN NN     12

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

CTCTTCNNNN     10

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

GAATGCN     7

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

ACCTGCNNNN NNNN     14

( 2 ) INFORMATION FOR SEQ ID NO:10:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

GGATCNNNNN                                             10

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

GCAGCNNNNN NNNNNNN                               17

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

GTCTCNNNNN                                             10

( 2 ) INFORMATION FOR SEQ ID NO:13:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

ACTGGN                                                           6

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

GGATGNNNNN NNNNNNNN                             18

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:15:

GACGCNNNNN NNNNN                                   15

( 2 ) INFORMATION FOR SEQ ID NO:16:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (xi) SEQUENCE DESCRIPTION: SEQ ID NO:16:

GGTGANNNNN NNN  13

(2) INFORMATION FOR SEQ ID NO:17:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:17:

GAAGANNNNN NNN  13

(2) INFORMATION FOR SEQ ID NO:18:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO:18:

GAGTCNNNNN  10

(2) INFORMATION FOR SEQ ID NO:19:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (xi) SEQUENCE DESCRIPTION: SEQ ID NO:19:

GCATCNNNNN NNNN  14

(2) INFORMATION FOR SEQ ID NO:20:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (xi) SEQUENCE DESCRIPTION: SEQ ID NO:20:

CCTCNNNNNN N  11

(2) INFORMATION FOR SEQ ID NO:21:

(i) SEQUENCE CHARACTERISTICS:
       (A) LENGTH: 90 base pairs
       (B) TYPE: nucleic acid
       (C) STRANDEDNESS: double
       (D) TOPOLOGY: circular (ii) MOLECULE TYPE: cDNA (xi) SEQUENCE DESCRIPTION: SEQ ID NO:21:

AGGAACCAAA CTGACTGTCC TAGGATAGAA GGAGATATAT CATGAAAAAG ACAGCTGGCG  60

CAGGCCGAGG TGACCCTGGT GGAGTCTGGG  90

(2) INFORMATION FOR SEQ ID NO:22:

(i) SEQUENCE CHARACTERISTICS:
(A) LENGTH: 58 base pairs
(B) TYPE: nucleic acid
(C) STRANDEDNESS: single
(D) TOPOLOGY: linear (xi) SEQUENCE DESCRIPTION: SEQ ID NO:22:

ATTAGAAGAC TACTCCNNNN NNNNNNNNN NNNNNNGAG GTGACCCTGG TGGAGTCT   58

(2) INFORMATION FOR SEQ ID NO:23:

(i) SEQUENCE CHARACTERISTICS:
(A) LENGTH: 58 base pairs
(B) TYPE: nucleic acid
(C) STRANDEDNESS: single
(D) TOPOLOGY: linear (xi) SEQUENCE DESCRIPTION: SEQ ID NO:23:

AATTGAAGAC ATGGAGNNNN NNNNNNNNNN NNNNNTCCT AGGACAGTCA GTTTGGTT   58

(2) INFORMATION FOR SEQ ID NO:24:

(i) SEQUENCE CHARACTERISTICS:
(A) LENGTH: 94 base pairs
(B) TYPE: nucleic acid
(C) STRANDEDNESS: double
(D) TOPOLOGY: circular (ii) MOLECULE TYPE: cDNA (ix) FEATURE:
(A) NAME/KEY: CDS
(B) LOCATION: 2..94

(xi) SEQUENCE DESCRIPTION: SEQ ID NO:24:

```
A GGA ACC AAA CTG ACT GTC CTA GGA CGG AAA TCG GGG CGG TCT ACC    46
  Gly Thr Lys Leu Thr Val Leu Gly Arg Lys Ser Gly Arg Ser Thr
  1               5                  10                  15

TCC CCT CTC CCA ATA AAA TTA GGG GAG GTG ACC CTG GTG GAG TCT GGG  94
Ser Pro Leu Pro Ile Lys Leu Gly Glu Val Thr Leu Val Glu Ser Gly
                20                  25                  30
```

(2) INFORMATION FOR SEQ ID NO:25:

(i) SEQUENCE CHARACTERISTICS:
(A) LENGTH: 31 amino acids
(B) TYPE: amino acid
(D) TOPOLOGY: linear (ii) MOLECULE TYPE: protein (xi) SEQUENCE DESCRIPTION: SEQ ID NO:25:

```
Gly Thr Lys Leu Thr Val Leu Gly Arg Lys Ser Gly Arg Ser Thr Ser
1               5                  10                  15

Pro Leu Pro Ile Lys Leu Gly Glu Val Thr Leu Val Glu Ser Gly
                20                  25                  30
```